United States Patent [19]

Di Domenico et al.

[11] Patent Number: 4,988,701

[45] Date of Patent: Jan. 29, 1991

[54] CYCLIC AMINO-THIOACETAL AMIDES, A PROCESS FOR THE PREPARATION THEREOF AND PHARMACEUTICAL COMPOSITIONS

[75] Inventors: Roberto Di Domenico; Carmelo A. Gandolfi; Silvano Spinelli; Bruno Lumachi; Odoardo Tofanetti; Sergio Tognella, all of Milan, Italy

[73] Assignee: Boehringer Biochemia Robin S.p.A., Milan, Italy

[21] Appl. No.: 453,390

[22] Filed: Dec. 15, 1989

Related U.S. Application Data

[63] Continuation of Ser. No. 214,345, Jul. 1, 1988, abandoned.

[30] Foreign Application Priority Data

Jul. 2, 1987 [IT] Italy ................................ 21159 A/87

[51] Int. Cl.$^5$ .................. C07D 277/04; C07D 277/06; A61K 31/425
[52] U.S. Cl. .................................... 514/255; 514/342; 514/365; 544/54; 544/367; 546/280; 548/200; 548/201; 548/146

[58] Field of Search ...................... 548/200, 201, 146; 546/280; 544/367; 514/365, 255, 342

[56] References Cited

U.S. PATENT DOCUMENTS 4,798,898 1/1989 Gandolfi .......................... 548/146

Primary Examiner—Robert Gerstl
Attorney, Agent, or Firm—Armstrong, Nikaido, Marmelstein, Kubovcik & Murray

[57] ABSTRACT

Cyclic amino-thioacetal amides of formula I

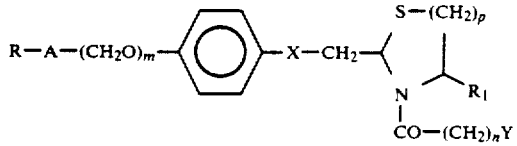

wherein X is O, S, p is 1 or 2, R and $R_1$ are optionally esterified hydrogen or carboxy, A is a single bond, methylene or ethylene, m is zero or 1, n is an integer 1 to 7 and y is a imidazole or β-pyridylmethyl residue.

Compounds I have valuable therapeutic properties.

6 Claims, No Drawings

CYCLIC AMINO-THIOACETAL AMIDES, A PROCESS FOR THE PREPARATION THEREOF AND PHARMACEUTICAL COMPOSITIONS

This application is a continuation of application Ser. No. 214,345 filed July 1, 1988 now abandoned.

The present invention relates to amino-thioacetal amides, to a process for the preparation thereof and to pharmaceutical and veterinary compositions containing them.

The compounds of the invention have general formula I

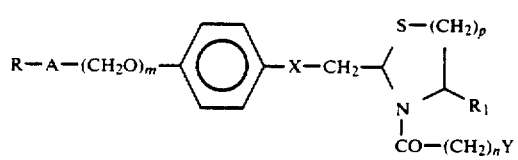

wherein:

R and $R_1$ are independently a H atom or a free carboxy group or an esterified $CO_2Ra$ group;

A is a single bond, a cis or trans —HC=CH—, a —C≡C—, a methylene or a —$CHG_2$—$CH_2$— group;

Y is a substituent selected from the group consisting of $X_1$—CO—Re, $CO_2Ra$, $CONRbRc$, imidazol-1-yl, 3-pyridyl, —$X_1$—$(CH_2)n$—Rd;

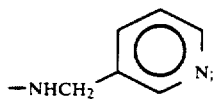

Ra is hydrogen or $C_1$-$C_5$ straight or branched alkyl;

Rb and Rc are H, $C_1$-$C_5$ alkyl, 2-dimethylamino-ethyl, 2-diethylamino-ethyl,

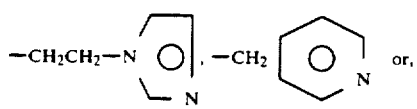

taken together with the nitrogen atom to which they are bound, form a 4-($C_1$-$C_5$-alkyl)piperazin-yl ring;

Rd is hydrogen, $C_1$-$C_5$ straight or branched alkyl,

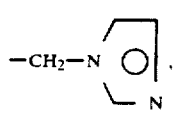

3-pyridyl, $CO_2Ra$ o $CONRbRc$;

Re is $C_1$-$C_5$ straight or branched alkyl, or phenyl;

X and $X_1$ are independently oxygen or sulfur;

m is zero or 1, p is an integer 1 to 2;

n is an integer 1 to 7.

The present invention also relates to the addition salts of compounds of formula I with pharmaceutically or veterinaryly acceptable base or acids, as well as to enantiometers, racemates, diastereoisomers or mixtures thereof, of compounds of formula I.

Typical examples of pharmaceutically acceptable acids are organic acids such as formic, acetic, propionic, tartaric, fumaric, maleic, malic, malonic, benzoic, salicylic, methanesulfonic, glutamic acids; inorganic acids such as nitric, sulforic, phosphoric, hydrochloric and hydrobromic acids. Typical examples of pharmaceutically acceptable bases are alkali and alkali-earth metal cations or ammonium cations, organic bases such as straight or cyclic aliphatic amines, e.g. methylamine, dimethylamine, diethylamine, trimethylamine, N-methyl-N- hexylamine, tromethamine, α-phenyl-ethylamine, piperidine, morpholine, piperazine, pyrrolidine and alkyl derivatives of the latter four bases, mono-, di- and tri-alkyl ethanolamines, galactamine, N-methylglucamine, N-alkyl-glucosamine, and amino acids such as lysine, arginine, glycine.

The enantiomers can be obtained by resolution of the racemates according to known methodes.

Preferred compounds of the invention are those in which the group R—A—$(CH_2O)_m$ is methoxy, carboxyl, ethoxycarbonyl, ethoxycarbonylmethoxy, carboxymethoxy, methoxycarbonylvinyl or allkyloxy and $R_1$ is hydrogen, carboxyl, methoxycarbonyl or ethoxycarbonyl; or those in which X is an oxygen atom, $X_1$ is a sulfur atom, R is a free or esterified carboxy group and $R_1$ is hydrogen; or those in which A is a single bond, R is hydrogen or a carboxy group, X is an oxygen atom and $R_1$ is an hydrogen atom.

Specific examples of the compounds of the invention are:

2-(4-methoxyphenoxymethyl)-3-ethoxycarbonylacetyl-thiazolidine 2-(4-methoxyphenoxymethyl)-3-(imidazol-1-yl)-acetylthiazolidine 1-N-(3'-pyridyl-methyl), 2N-[2'(4''-methoxyphenoxymethyl)-thiazolidine-3'-yl]-malondiamide 2-(4-methoxyphenoxymethyl)-3-(β-pyridylmethylthio)acetylthiazolidine 2-(4-allyloxyphenylthiomethyl)-3-(imidazol-1-yl)-acetyl-4-carbethoxy-thiazolidine 2-(4-carboxy-phenoxymethyl)-3[7(imidazol-1-yl)heptanoyl]-thiazolidine 2-(4-methoxy-phenoxymethyl)-3(ethoxycarbonyl-acetyl)-2-H-tetrahydro-thiazine.

The compounds of the invention are prepared by reacting a cyclic amino-thioacetal of formula (II)

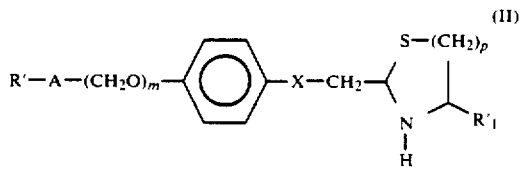

wherein R' and $R'_1$ are independently H or $CO_2R'a$, R'a is a $C_1$-$C_5$ alkyl and A, m, p, X are as above defined, with an acylating species of formula (III)

P—CO—T (III)

prepared from a carboxylic acid of formula (IIIa)

P—COOH (IIIa)

wherein R is Cl, Br, $N_3$, imidazol-1-yl or a OCOD group, in which D is a $C_1$-$C_5$-alkyl or benzyl, whilst P is a —$(CH_2)n$—Y, —$(CH_2)_n$Hal and —CH=$CH_2$ group, in which Hal is a halogen atom (Cl, Br, I) or the residue of a sulfonic ester, such as mesylate, p-toluenesulfonate, benzenesulfonate and n and Y are as above defined, to give a compound of formula (Ia)

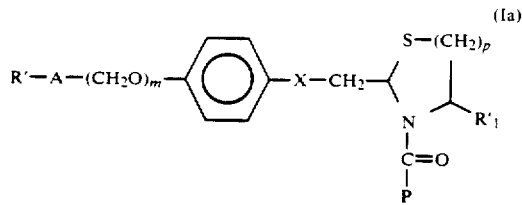

wherein R', R'₁, P, m, p, x are as above defined.

Compounds of formula Ia in which P is $(CH_2)_n$ Hal or $-CH=CH_2$ can be then transformed into compounds of formula (Ib)

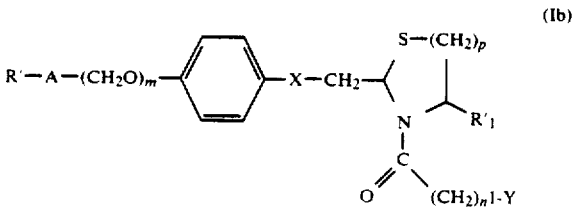

in which R', A, m, p, X and Y are as above defined, $n^1$ is an integer 1 to 7, preferably 1 or 2, by reaction with an appropriate nucleophilic compound such as 1-imidazolyl or β-pyridyl-methylamine salts, thiocarboxylates of formula Re—CO—S⁽⁻⁾ or alchoholates or thiolates of formula Rd $(CH_2)_n$—X,⁽⁻⁾ (Rd, Rd and X' as above defined).

Compounds of formula (Ic)

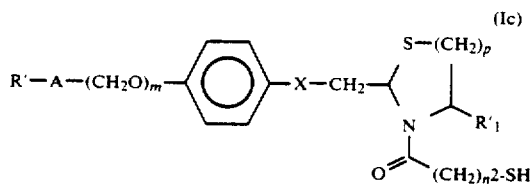

wherein R', R₁', A, m, x, p are as above defined and $n_2$ is an integer 1 to 2, can be obtained by mild, selective hydrolysis from the corresponding acethylthio and benzoylthio derivatives with ammonia. The same compounds Ic can optionally be reacted, in the presence of bases, with a compound of the formula IV

In which Rd and Hal are as above defined, to obtain a compound of formula I in which Y is a group of formula —S—CH₂—Rd.

The resulting compounds can then be optionally subjected to subsequent hydrolysis of the ester groups, optical resolution and/or salification reactions.

Under the experimental point of view, acylation reaction of a cyclic amino-thioacetal of formula II with the reactive form of a carboxylic acid of formula III is a classic reaction of formation of a tertiary amide, accordingly the reaction conditions are the ones well-known in the techniques for the preparation of this class of compounds. For example, the reaction is carried out in an inert solvent, in the presence of a counter-base acceptor of the leaving group T, such as an inorganic base (an alkali carbonate or bicarbonate) or an organic aliphatic tertiary (such as triethylamine) or aromatic (pyridine or a dialkylaniline) base. The acylating species and the counter-base will be used in a stoichiometric ratio or in a slight excess with respect to the cyclic amino-thioacetal. The reaction can be effected in a wide range of temperatures and reaction times, depending on the reactivity of the acylating species.

The preparation of the reactive acylating species of formula III is carried out using conventional, well-known process such as formation of mixed anhydrides or acyl chlorides; alternatively; the acylating species is prepared "in situ" using bis-oxazolydine-phosphoryl chloride and a carbodiimide, particularly, dicyclohexylcarbodiimide, as the species activating the carboxy group.

Conversion of a compound of formula Ia, in which P in a —$(CH_2)_n$—Hal group, into a compound of formula I, by reaction with a sodium and potassium thioacid salt, is preferably carried out under phase transfer conditions, between a solution of a compound of formula Ia in an inert organic solvent and an aqueous solution of the thioacid salt; said reaction conditions apply as well to the alkylation of said compounds of formula Ia with a thiol of formula V

or to the reaction with imidazole. The inert solvent can be an ester, such as ethyl acetate, an halogenated solvent such as dichloroethane, chloroform or an hydrocarbon such as cyclohexane, benzene or mixtures thereof.

Alternatively, alcoholates, thiolates or thioacid salts can be reacted in alcoholic solvents such as ethanol, propanol, tert-butanol, using equimolecular amounts or a slight excess of the reagent, for a time from a few minutes to some hours, at a temperature ranging from room temperature to the reflux temperature of the solvent, sometimes from 0° C. to room temperature consistently with solidification temperature of the solvent.

Optional conversion of the compound of formula Ia, in which P is a —$CH=CH_2$ group, is carried out by addition of the above mentioned nucleophlic agents, according to traditional Michael addition, to an acrylamide.

Optional conversion of a compound of formula Ib, in which Y is selected from the group of S—COCH₃ or S—CO—C₆H₅, into a compound of formula Ib, in which Y is S—CH₂Rd, is effected by selective hydrolysis of a thioester group, by reaction with an aqueous solution of ammonia and/or an aliphatic primary amine having 1 to 4 carbon atoms, in a water-miscible inert solvent, or under transfer conditions, to give a compound of formula Ib in which Y is a free thiol, followed by reaction of said free thiol with a compound of formula IV, under the same reaction conditions as above described.

Compounds of general formula II are new and subject of the invention. They are preferably prepared by an amino-thioacetalization reaction of aldehydes of general formula

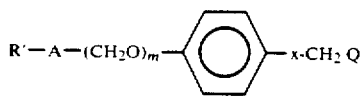

wherein R', A, m, x are as above defined and Q is CHO, with an aminothiol of formula VII

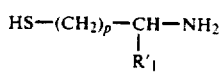

in which p and $R'_1$ have the above described meanings.

Aminothiols of formula VII are commercialy available compounds (cysteine, homocysteine and esters thereof, cysteamine, homocysteamine) in form both of free bases and salts. Amino-thioacetalization reaction is effected by admixing stoichiometric amounts of the aldehyde and the aminothiol at room temperature, in an inert solvent such as an hydrocarbon, e.g. benzene, an ester e.g. ethyl acetate, or an alcohol, e.g. ethanol. If the aminothiol is in form of a salt thereof, the reaction is carried out in the presence of stoichiometric amounts of an aqueous solution of a base, preferably an alkali carbonate or bicarbonate.

Aldehydes of general formula VI can be prepared from phenols and thiophenols of general formula VIII

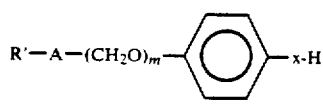

(wherein R', A, m and X are as above defined), by reaction of a sodium or potassium phenolate or thiophenolate thereof with an alkyl derivative of formula IX $Hal-CH_2-Q'$ (IX)

in which Hal is as above defined, and Q' is selected from the group consisting of

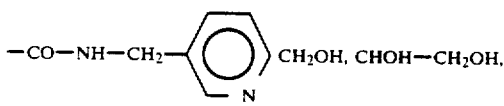

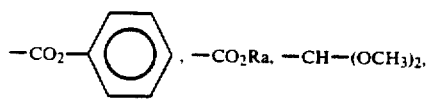

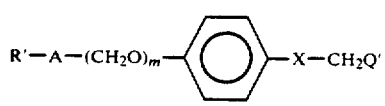

to give a compound of formula VIa

wherein R', A, m, x, and Q' are as above defined, which can then be transformed into an aldehyde of formula VI When $Q'=CH_2OH$, preparation of VI is preferably effected using Moffat reaction (selective oxidation in dimethylsulfoxide with a carbodiimide), whilst when Q' is $CHOH-CH_2OH$, the preferred reaction is the oxidative cleavage with a periodate or with HgO and $I_2$ (according to J. Chem. Soc. (C), 383 (1969)). When Q' is $CO_2-C_6H_5$, the preferred method is the selective reduction to formyl with lithium-tri-tert-butoxy-alluminium hydride (Theilheimer Synth. Method. 21, 89). When Q' is

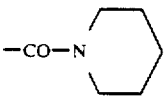

the preferred method is the reaction with $POCl_3$ in benzene, followed by treatment with zinc powder, according to J. Chem. Soc. Chem. Comm. 594 (1976).

When $Q'=CO_2H$, the carboxy group can be converted into the mixed anhydride, imidazolide or acyl chloride, then transformed into the aldehyde by reduction with $NaBH_4$, optionally in the presence of the complex $CdCl_2$-dimethylformamide [J. Chem. Soc., Chem. Comm. 354 (1978), Synth. COmm. 12, 839 (1982)].

When Q' is an acetyl group, this is preferably hydrolyzed to aldehyde in the presence of diluted aqueous acids, or, if desired, it is subjected to a trans-acetalization reaction with an aminothiol of formula VII.

In the preparation of compounds of formula VI, in which X is oxygen, the preferred method is the reaction of a phenol with 1-chloro-propane-2,3-diol to give a compound of formula VIa, which is then reacted with a periodate, such as sodium periodate. When X is S, the preferred method is the reaction of a thiol of formula VII with phenyl-chloroacetate, followed by selective reduction to aldehyde of the phenyl ester, by means of lithium tri-tert-butoxy-alluminium hydride.

Alternatively, the following reaction scheme summarizes a general synthesis method for the preparation of a compound of general formula VI, to give a compound of formula II

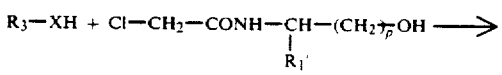

(VIII)                (IXa)

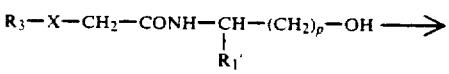

(VIb)

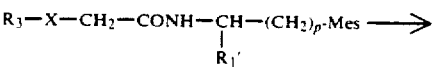

(VIc)

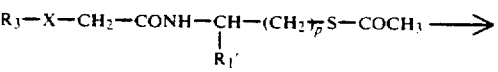

(VId)

-continued

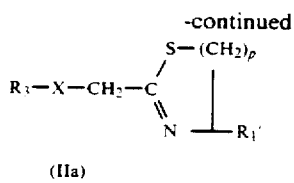

(IIa)

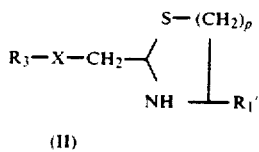

(II)

(wherein $R_3 = R'-A-(CH_2O)_m-$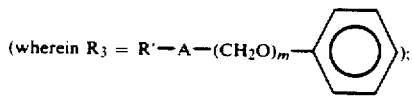);

According to the above reported scheme, a phenol and/or a thiol of formula VIII is reacted with the α-chloroacetamide of an aminoalcohol of formula $$HO-(CH_2)p-CH-NH_2 \quad\quad (VIIb)$$
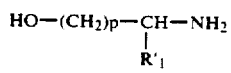

to give a phenyl and/or a thiophenyl ether of formula VIb, which is then reacted with methanesulfonyl chloride to give a mesylate of formula VIc. The subsequent reaction with a thioester alkali salt (such as potassium thioacetate) transforms the compound into the thioester VId, which is then converted into the corresponding imino-thioester of formula IIa with gaseous HCl. Selective reduction with sodium borohydride eventually gives cyclic amino-thioacetal of formula II.

The compounds of the invention have valuable properties, when compared with corresponding ortho-substituted analogs, some of which have been described in EP-A-169.581. For example, acute toxicities in rats and mice, by the oral, intraperitoneal and intravenous routes, expressed as LD$_{50}$ values, turned out to be generally higher than 0,8-1 g/kg, for the compounds of the invention.

The compounds of the invention, after oral administration, further reduce paracetamol and carbon tetrachloride induced hepato-toxicities in the mouse, protect hematopoietic system against damages by exposition to radiations, and protect against development of pulmonary adenomas and forestomach tumors induced by benzo[a]pyrene in ICR/Ha mice.

Treatment of rats by oral route with the compounds of the invention induces a substantial increase in gluathion cell levels as well as of detoxyifying enzymes such as glutathion S-transferase, UDP-glucuronyl transferase and epoxy hydrolase.

Besides the glutathion levels, also the levels of the enzymes involved in the maintaining of the reduced glutathion reserves, such as glutathion reductase, glucose-6-phosphatase and 6-phosphogluconatedehydrogenase, turned out to be increased.

The compounds of the invention, moreover, can inhibit enzyme thromboxane-A2-synthetase; consequently, when administered by the oral route, they protect rats and mice against sudden death induced by administration (in bolus) of arachidonic acid or by an ADP and collagen mixture.

After oral administration, compounds I protect also gastric mucosa of rats from erosion induced by stress and by cold, substantially induced by the method of Togagi and Okabe (see, for instance, Jap. J. of Pharmacol. 18, 9, 1968).

A similar cytoprotective effect of gastric mucosa was also evidenced in stomach ulcers induced by endogenous agents such as serotonin or by external agents such as ethanol, phenylbutazone, indometacin and acetylsalicylic acid.

Moreover, the compounds of the invention protect against bronchospasm induced in guinea pigs by allergens or by ovalbumin.

Treatment of rats with the compounds of the invention, besides proving a cytoprotective action of gastric mucosa, also evidences a favourable secretolytic effect also on bronchial mucus, as proved by an increased red phenol and fluoresceine secretion in comparison with untreated controls. Similar results were obtained using mice as test animals.

Thus, the compounds of the invention are particularly suited as cytoprotective agents against oxidative injuries, as lipooxygenase inhibitors, as normalization agents of a pathological bronchial mucus and as cytoprotectors of gastic mucosa.

The compounds of the invention can be administered both to human and animals, for the treatment of obstructive pulmonary conditions, by different routes: orally (in form of tablets or capsules, or in liquid form in as drops or syrups); rectally (suppositories); intravenously (said administration route being preferred under emergency conditions); intramuscularly or subcutaneously; by inhalation (in form of aerosols or solutions for nebulization); by insufflation (in form of powders); finally in form of sterile implantations to obtain a prolonged action.

Dosages will range from 0,005 to 4 mg/kg and will be administered 1 to 4 times a day, the specific dosage varying depending on the age, weight and conditions of the patient, as well as on the administration route.

The pharmaceutical and veterinary compositions containing the compounds of the invention can be conventionally prepared and contain usual carriers or diluents. For example, isotonic sterile aqueous solutions are preferred in case of intravenous injections and of infusions; sterile solutions in aqueous or non-aqueous media are preferred in case of subcutaneous or intramuscular injections; sterile tablets or silicon gum capsules containing or impregnated with the compound are preferred in case of tissue implantations.

Conventional carriers or diluents are, for example: water, gelatin, lactose, dextrose, saccharose, mannitol, sorbitol, cellulose, carboxymethylcellulose and the like, talc, stearic acid, calcium and magnesium stearates, glycol, starch, gum arabic, tragacanth gum, alginic acid and alginates, lecithin, polysorbate, vegetal oils, etc.

For the administration through nebulization, suspensions or solutions of the compounds of the invention can be used, preferably in salified form as hydrochloride, nitrate, maleate, tartrate, camphosulfonate, etc., in water. Alternatively, the pharmaceutical formulation can be a suspension of the compounds of the invention in one of the usual liquefied propellers, such as dichlorodifluoromethane or dichlorotetrafluoroethane: the compounds of the invention in this case will be administered by means of a container such as an aerosol bomb. If the compound is not soluble in the propeller, a solvent such ad dipropylene glycol, propylene glycol, ethanol and mixtures thereof and/or an emulsifier can be added.

The invention will be illustrated by the following non-limiting examples.

EXAMPLE 1

30 g of sodium ethylate was added to a solution of 50 g of 4-methoxy-phenol and 37 ml of 1-chloro-propane-2,3-diol in 300 ml of ethanol; the mixture was refluxed for 3 hours under stirring and, after filtration of NaCl, was concentrated to small volume to give an oily mass. The residue was partitioned between ethyl ether and water, the organic phases were washed with 5% aqueous sodium hydroxide, water, 20% $NaH_2PO_4$ and water and dried over sodium sulfate. Upon concentration 60 g of 3-(4'-methoxy-phenoxy)-propane-1,2-diol separated, m.p. 55°-56° C.

After strong stirring, this diol was added portionwise to a solution of 65 g of sodium periodate in 600 ml of water, during 30 minutes. Stirring was continued for 2 more hours at room temperature, to obtain the complete oxidation of the diol.

The reaction mixture was then diluted with 1,2 more l of water and partitioned with ethyl acetate (800, 250, 250 ml). The organic phases were combined, worked with 3 ×50 ml of 5% aqueous NaCl, dried over $Na_2SO_4$. A sample from the reaction was evaporated to dryness to give an analytic of 2-(4-methoxy-phenoxy)-ethanal.

The aldehyde solution in ethyl acetate was added with 33,5 g of potassium bicarbonate and, under stirring, with a solution of cysteamine hydrochloride (37,5 g) in 70 ml of water.

The mixture was kept under stirring overnight; the organic phase was separated, washed repeatedly with water, dried over sodium sulfate. After evaporation of the solvent, the residue (54 g) was crystallized from ethyl ether to give 46,8 of 2(4-methoxy-phenoxymethyl)-thiazolidine, m.p. 54°-55° C.

EXAMPLE 2

Using in the procedure of Example 1, instead of cysteamine hydrochloride, one amino-alkylthiol selected from the group consisting of 1-amino-3-mercapto-propane;
1-amino-4-mercapto-butirryc acid(homocysteine);
homocysteine ethyl ester;
cysteine ethyl ester;
cysteine methyl ester;
the following compounds were prepared:
2-(4-methoxy-phenoxymethyl)-2H-tetrahydro-1,3-thiazine
2-(4-methoxy-phenoxymethyl)-2H-tetrahydro-4-carboxy-1,3-thiazine
2-(4-methoxy-phenoxymethyl)-2H-tetrahydro-4-ethoxycarbonyl-1,3-thiazine
2-(4-methoxy-phenoxymethyl)-4-carbomethoxy-thiazolidine
2-(4-methoxy-phenoxymethyl)-4-carboxy-ethoxy-thiazolidine.

EXAMPLE 3

Using in the procedure of examples 1 and 2, ethyl 4-hydroxybenzoate and ethyl 4-hydroxy-phenoxyacetate instead of the 4-methoxy derivative, and cysteamine and 1-amino-3-mercapto propane the following compounds were prepared;

3-[4-carboethoxy-phenoxy]-propane-1,2-diol
3-[4-(ethoxycarbonylmethoxy)phenoxy]-propane-1,2-diol
2-[4-(carboethoxy)]phenoxy-ethanal
2-[4(ethoxycarbonylmethoxy)]phenoxy-ethanal
2-[4(carboethoxy)phenoxymethyl]thiazolidine
2-[4(carboethoxy)phenoxymethyl]-2H-tetrahydro-1,3-thiazine
2-[4(ethoxycarbonylmethoxy)phenoxymethyl]-2H-tetrahydro-1,3-thiazine
2-[4(ethoxycarbonylmethoxy)phenoxymethyl]-thiazolidine.

EXAMPLE 4

A solution of chloroacetyl chloride (1,22 ml) in dichloromethane (6 ml) was added dropwise to a solution of 3,82 g of 2-(4-methoxy-phenoxymethyl)-4-carboethoxythiazolidine and ethylamine (2,1 ml) in dichloromethane (30 ml), under stirring and cooling at about 0° C.

Stirring was continued for 3 hours. The reaction mixture was washed repeatedly with water (3 × 10 ml), 25% aqueous $NaHCO_3$, then with water (2 × 10 ml) till neutral.

After drying over $Na_2SO_4$, the solution was evaporated to dryness to obtain 3,3 g of 2-(4-methoxy-phenoxymethyl)-3-chloroacetyl-4-carboethoxy-thiazolidine after crystallization from ethyl ether; m.p. 69°-71° C.

A solution of 3 g of said compound in 30 ml of dichloromethane was added with 2,7 g of imidazole and 0,01 g of tetrabutylammonium bromide. The mixture was refluxed for 6 hours under stirring then, after cooling, the organic phase was repeatedly washed with water and dried over $Na_2SO_4$. After evaporation of the solvent, by crystallization from ethanol 2,1 g of 2-(4-methoxyphenoxymethyl)-3[2'(imidazol-1'-yl)acetyl]4-carboethoxythiazolidine, m.p. 99°-103° C., separated.

EXAMPLE 5

Using, in the procedure of example 4,2-(4-methoxyphenoxymethyl)-2H-tetrahydro-4-carboethoxy-1,3-thiazine the following compounds were obtained:

2-(4-methoxyphenoxymethyl)-2H-tetrahydro-3-chloroacetyl-4-carboethoxy-1,3-thiazine;
2-(4-methoxyphenoxymethyl)-2H-tetrahydro-3[(2'(imidazol-1'-yl)acetyl]-4-carboethoxy-thiazine.

EXAMPLE 6

A solution of 26 g of potassium bicarbonate in 55 ml of water was added under storing stirring to a solution of 2-(4-methoxy-phenoxymethyl)thiazolidine (54,5 g) in 550 ml of ethyl acetate cooled at 0°-5° C. The mixture was added with a solution of α-chloro-acetylchloride (19,2 ml) in ethyl acetate (50 ml) for 1 hour, under strong stirring and external cooling. Stirring was continued for 2 more hours, then the phases were separated. After washing of the organic phase with water, 5% aqueous $NaHCO_3$ and water, and drying over $Na_2SO_4$, the mixture was evaporated to dryness to give 54,5 g of 2-(4-methoxy-phenoxymethyl)-3-α-chloroacetyl-thiazolidine, m.p. 51°-53° C. (from isopropyl alcohol).

A solution of 25 g of the α-chloroacetyl derivative in dichloromethane (100 ml) was added with 14 g of imidazole, 1,2 g of tetrabutylammonium bromide and 25 ml of a 20% aqueous solution of sodium hydroxide, under strong stirring. Stirring was continued for 8 hours, then the phases were separated and the organic phase was washed with water till neutral, dried and evaporated to dryness. By crystallization from ethyl acetate, 22,5 g of 2-(4-methoxyphenoxy-methyl)-3[2'(imidazol-1'-yl)acetyl]4-thiazolidine was obtained, m.p. 126°-128° C.

To a solution of 22 g of the compound in 440 ml of ethanol at 50° C., a solution of 10,1 g of l-tartaric acid in 80 ml of water-ethanol (3:1) was added in one time, keeping said temperature of 15 minutes: during the subsequent cooling phase, formation of a crystalline precipitate began, which was complete after 2 hours at 15°-20° C. After filtration and drying under vacuum (16 mmHg, 80° C.), 28,6 g of 2-(4-methoxyphenoxy-methyl)-3 [2'(imidazol-1'-yl)acetyl]4-thiazolidine l -tartrate was obtained, m.p. 146°-148° C.

EXAMPLE 7

3 g of 2-(4-methoxyphenoxymethyl)-3-chloroacetyl-1,3-thiazolidine in an ethyl acetate (30 ml) solution was treated with a KSCOCH$_3$ solution (1,25 g) in H$_2$O (5 ml) at room temperature, under strong stirring, to obtain 2-(1-methoxy-phenoxymethyl)-3-acetyl-thioacetyl-1,3-thiazolidine which was recovered from the organic phase after washing with H$_2$O, drying over Na$_2$SO$_4$ and evaporation of the solvent under reduced pressure. The residual oil (3,1 g) crystallized from ethyl acetate, m.p. 108°-110° C.

EXAMPLE 8

A solution of 0.56 g of sodium methylate is MeOH (5 ml), cooled at 0° C., was treated with 0,71 ml of ethanethiol (CH$_3$CH$_2$SH). After 10 minutes, a solution of 3 g of 2-(4-methoxyphenoxymethyl)-3-α-chloroacetyl-1,3-thiazolidine in 10 ml MeOH was dropped into the mixture. After 30 minutes, the solvent was removed under reduced pressure and the residue was partitioned between 30% NaH$_2$PO$_4$ and ethyl acetate. The organic phase was washed with water, dried over Na$_2$SO$_4$ and concentrated to dryness to yield 2,9 g of 2-(4-methoxyphenoxymethyl)-3-ethylmercaptoacetyl- 1,3-thiazolidine after crystallization from isopropyl ether, m.p. 98°-110° C.

EXAMPLE 9

To a solution of 2-(4-methoxyphenoxymethyl)-2H-tetrahydro-1,3-thiazine (5,6 g) in 60 ml of ethyl acetate, under strong stirring and cooling to 0°-8° C., a solution of KHCO$_3$ (2,2 g) in 6 ml of H$_2$O was added, then, during 15 minutes, a solution of ethyl malonylchloride (2,5 ml) in ethyl acetate (7 ml). Stirring was continued for 2 hours, the aqueous phase was removed and the organic phase was washed with water, 2N H$_2$SO$_4$ and water till neutral, dried over sodium sulfate and evaporated to dryness; by crystallization from ethyl ether 4,8 of N-[2(4-methoxyphenoxymethyl)-2H-tetrahydro-1,3-thiazine-3-yl]-monomalonamide ethyl ester was obtained.

4,2 g of [2(4-methoxyphenoxymethyl)-2H-tetrahydro-1,3-thiazine-3-yl] monoamido malonic acid sodium salt was obtained by reaction of a solution of 4,7 g of the above ethyl ester in EtOH (50 ml), with 15 ml of aqueous N NaOH for 1 hours at room temperature and filtration of the crystalline precipitate which separated after cooling to 0°-5° C. By acidification from 2N H$_2$SO$_4$ of a solution of the above salt in 25 ml of water and subsequent filtration of the precipitate, 1,6 g of [2(4-methoxyphenoxymethyl)-2H-tetrahydro-1,3-thiazine-3-yl]monoamido malonic acid was obtained.

1,5 g of the acid and 0,6 ml of 4-methyl-piperazine were dissolved in ethyl acetate (20 ml), cooling to 0°-5° C., and the mixture was added with a solution of 1,05 g of dicyclohexylcarbodiimide in ethyl acetate (5 ml), kept at 0° C. for 1 hour, then heated to 40° C. for 3 hours. The excess reagent was decomposed by addition of a 6% oxalic acid aqueous solution, the dicyclohexylurea precipitate was filtered off and washed with water. The washings combined with the solution were dried over sodium sulfate and evaporated to dryness. Upon crystallization from ethyl ether, 1,42 g of N(4-methylpiperazin-1-yl)-, N'[2(4-methoxyphenoxymethyl)-2H-tetrahydro-1,3-thiazine-3-yl)-monomalonamide was obtained.

EXAMPLE 10

Using in the procedure of Example 9 2-(4-methoxyphenoxymethyl)thiazolidine instead of 2-(4-methoxyphenoxymethyl)2H-tetrahydro-1,3-thiazine, N[2(4-methoxyphenoxymethyl)-thiazolidin-3-yl] monomalonamide ethyl ester, was prepared.

By heating to 40° C. for 20 hours under stirring a solution of 5 g of the above malonyl ethyl ester in 40 ml of a 33% solution of methylamine in ethanol, after filtration of the crystalline precipitate formed and crystallization from dichloromethane- ethyl acetate, 4,2 g of N-methyl-N[2(4-methoxy-phenoxymethyl)thiazolidine-3-yl)malonodiamide was obtained.

By an analogous procedure, refluxing a solution of 5 g of the above malonyl ester in 40 ml of ethanol with 4 g of 3-pyridylmethylamine for 8 hours, 4,2 g of N-β-pyridylmethyl,N'(2(4-methoxy-phenoxymethyl)-thiazolidinyl-3-yl)malonodiamide was obtained.

EXAMPLE 11

A solution of 3-pyridylcarbinol (30,5 ml) in dichloroethane (400 ml) was added with triethylamine (56 ml), then, under stirring and cooling to 0°-5° C., with a methanesulfonyl chloride (31,7 ml) in dichloroethane (50 ml) solution in about 1 hour. Stirring was continued for 40 minutes at 0°-5° C. The mixture was washed with water (2×100 ml), then, under vigorous stirring, a solution of potassium thioacetate (4,8 g) in 200 ml of water was added. Stirring was continued for 1 more hours, the phases were separated and, from the organic phase, after washing with water (2×50 ml), drying, decolorization with charcoal and evaporation of the solvent, 48 g of 3-pyridylmethylmercaptane acetate was obtained.

A solution of 6,2 g of said reagent and 11,2 of 2-(4-methoxyphenoxymethyl)-3-α-chloroacethyl-thiazolidine in ethanol (50 ml) was added with finely powdered potassium carbonate (10 g) and the mixture was kept under stirring for 16 hours. The residue was filtered off and the solution was evaporated under vacuum. The residue was partitioned between water and ethyl acetate; from the organic phase, after the usual working and evaporation of the solvent, 9,27 g of 2-(4-methoxyphenoxymethyl)-3-[8-β-pyridyl-3-thia-butanoyl)-thiazolidine was obtained.

EXAMPLE 12

To a suspension of 20 g of potassium carbonate in 60 ml of anhydrous dimethylformamide (DMF), 17,8 g of methyl trans-4-hydroxy-cinnamate was added. The mixture was heated to 60°-80° C. under strong stirring and slowly added with a solution of 17,5 g of phenyl α-chloroacetate in 17 ml of DMF, during 30 minutes. Stirring was continued for 4 hours, the excess solvent was distilled under reduced pressure; the residue was partition between water and ethyl acetate to give, after the usual working, 26,9 g of methyl trans-4(phenoxycarbonylmethoxy)cinnamate.

A solution of the above compound in anhydrous tetrahydrofuran (THF) (50 ml) was added under stirring to a suspension of 22 g of lithium-triterbutoxy aluminum in 150 ml of anhydrous THF during 5 minutes. Stirring was continued for 2 hours at 0°-5° C., then, keeping temperature of the reaction mixture at 0°-5° C., 5 ml of 4N $H_2SO_4$ was added to destroy the excess reactive. The formed salts were filtered off, the eluate was evaporated under vacuum, the residue was taken up in ethyl ether and, after the usual working of the organic phase (washing with 5% aqueous $NaHCO_3$, water, drying), 17,9 g of methyl 4-formylmethoxy-cinnamate was obtained, which was transformed according to the process of Example 1, by reaction with cysteamin hydrochloride (9,2 g) and with a $KHCO_3$ aqueous solution (8,2 g) in ethyl acetate, to give 18,2 g of methyl 4[(thiazolidine-2-yl)methoxy]cinnamate.

Analogously, starting from 4-allyloxy-thiophenol, 2[4-alyloxy-phenyl-thiomethyl]thiazolidne was prepared.

EXAMPLE 13

A solution of triethylamine (6,5 ml) and 7-(imidazol-1-yl)-heptanoic acid (4,5 g) in dichloroethane (50 ml) was added with 5,6 of 2-[4-carboethoxy-phenoxymethyl]-thiazolidine. 5,8 g of bis-oxazolidinon-phosphoryl chloride was added under stirring, cooling to 0°-5° C. After 3 hours the organic phase was treated with a $NaHCO_3$ saturated aqueous solution, washed with water and evaporated to dryness to give, after crystallization from ethyl ether, 6,22 of 2-[4-carboethoxy-phenoxymethyl]-3[(7'-imidazol-1-yl-)hepanoyl]thiazolidine.

A suspension of the above compound (1,5 g) in 10% aqueous potassium carbonate was refluxed till complete dissolution. The aqueous solution, after cooling, was extracted with ethyl ether. The organic phase was discarded, the aqueous phase was added with a $NaH_2PO_4$ excess and the crystalline solid which separated was filtered to give 1,05 g of 2-[4-carboxy-phenoxymethyl]-3[7'(imidazol-1-yl)-heptanoyl]-thiazolidine.

EXAMPLE 14

A solution of 2,7 g of 2-[4'-carbethoxy-phenoxymethyl]-1,3-thiazolidine was reacted with 0,93 g of acryloyl chloride in ethyl acetate (25 ml) in the presence of 1,1 g of potassium carbonate and some water to give, according to the procedure of Example 1, the corresponding acrylamide (3 g of 2-(4'-carboethoxyphenoxymethyl)-3-acryloyl-1,3-thiazolidine).

In an analogous way 2-(4-methoxy-phenoxy-methyl)-3-acryloyl-thiazolidine and 2-(4-methoxyphenoxymethyl)-3-acryloyl-2H-tetrahydro-1,3-thiazine were prepared.

Solutions of the above compounds (0.02 molar equivalents) in absolute ethanol (100 ml) were added at room temperature with 0,002 molar equivalents of a base, such as imidazole or β-pyridyl-ethylamine, and kept under stirring for 8 to 12 hours at room temperature. Solvent was evaporated under vacuum and the oily residue was partitioned between water and ethyl acetate. The organic phase was separated, dried and evaporated to dryness to give a vitreous mass which was dissolved in acetone (80 ml) and added with one molar equivalent of a solution of a carboxylic acid, such as maleic acid, to crystallize the corresponding maleate.

The following compounds, in form of maleates, were thus prepared:
- 2-(4'-carboethoxyphenoxymethyl-3-(imidazol-1'-yl)propanoyl-1,3-thiazolidine;
- 2-(4'-carboethoxyphenoxymethyl-3-(β'-pyridylmethylamino) propanoyl-1,3-thiazolidine;
- 2-(4-methoxyphenoxymethyl)-3-(imidazol-1-yl)propanoylthiazolidine;
- 2-(4-methoxyphenoxymethyl)-3-(β'-pyridylmethylamino)propanoyl-thiazolidine;
- 2-(4-methoxyphenoxymethyl)-3-(imidazol-1-yl)propanoyl-2H-tetrahydro-1,3-thiazine;
- 2-(4-methoxyphenoxymethyl)-3-(β'-pyridylmethylamino)propanoyl-2H-tetrahydro-1,3-triazine.

EXAMPLE 15

0.9 g di β-pyridylmethylmercaptane (obtained for example by hydrolysis of 3-pyridylmethylmercaptane acetate prepared in Example 9 with finely powdered $K_2CO_3$ in EtOH at room temperature) was added to a solution of 1,8 g of 2-(4-methoxyphenoxymethyl)-3-acryloyl-thazolidine in methanol (30 ml) containing 1-2 drops of a solution of Triton B in methanol. The mixture was stirred for 4 hours at 0°-10° C. and concentrated under vacuum. The oily residue was partitioned between water and ethyl acetate. From the organic phase, after the usual working, by evaporation of the solvent a residue was obtained, which was purified by silica gel chromatography, to give 1,32 g of 2-(4-methoxyphenoxymethyl)-3-[3'(β-pyridylmethylthio)propionyl]-thiazolidine.

The same compound was also obtained by reacting 2-(4-methoxyphenoxymethyl)-3-acryloyl-thiazolidine (11 g) in methanol (150 ml) with a thioacetic acid excess (10 ml) at 0°-5° C. for 2,5 hours. The reaction mixture was then neutralized by careful addition of a potassium carbonate aqueous solution and after evaporation of the alcohol under vacuum, the residue was partitioned between water and ethyl acetate. From the organic phase, by evaporation of the solvent, a residue was obtained which was chromatographed on silica gel (hexane: ethyl acetate 4:1) to give 9,4 g of 2-(4-methoxyphenoxymethyl)-3[(3'-acetylthio)propanoyl]-thiazolidine.

A solution of the above compound in methanol (80 ml) was added with a 10% ammonia solution in methanol (10 ml) at 0°-5° C., under inert gas atmosphere. After 4 hours, the mixture was concentrated under vacuum and diluted with water to give, after extraction with ethyl ether and the usual working of the organic phase, 6,8 g of 2-(4-methoxyphenoxymethyl)-3-[(3'-mercapto)propionyl]-thiazolidine.

A solution of said compound in methanol (20 ml) was added with sodium methylate (1,5 g), cooled to 0 C. and reacted with 5,2 g of β-pyridylcarbinol mesylate. After 3 hours at 0°-5° C., the reaction mixture was poured into an excess of a 15$NaH_2PO_4$ solution in water (80 ml). The precipitate was separated and extracted with ethyl ether. From the organic phase, after the usual working, 5,1 g of 2-(4-methoxyphenoxymethyl)-3[3'(β-pyridylmethylthio)propionyl]thiazolidine was obtained.

EXAMPLE 16

By reacting 2-[4-methoxyphenoxymethyl]-3-[3'-mercaptopropionyl)-thiazolidine with 2(imidazol-1-yl)-ethane-1-methanesulfonate (obtained by treating N-2-hydroxyethylimidazole (Yoshino et al. J.C.S. Perkin I (1977, 1266) with methanesulfonyl chloride in dichloroethane, in the presence of triethylamine) according to the procedure of Example 15, 2-[4-methoxyphenoxymethyl]-3[(3-imidazol-1-yl-ethyl-thio)propionyl]-thiazolidine was prepared.

EXAMPLE 17

A solution of 4-allyloxyphenylthioethanal (2 g) in ethanol (12 ml) was added with 1,65 g of ethyl L-2-amine-4-mercapto-butanoate. The mixture was left to stand for 2 hours at 15°–18° C. and 2,8 g of ethyl 2-(4-allyloxyphenylthiomethyl)-2H-tetrahydro-thiazine-4-carboxylate. Using in the same procedure 1,5 g of methyl L-2-amine-3-mercapto-propionate, 2,65 g of ethyl 2-(4-allyloxy-phenylthiomethyl)thiazolidine-4-carboxylate was obtained.

EXAMPLE 18

A solution of 1,8 g of ethyl 2-(4-allyloxyphenylthiomethyl)-2H-tetrahydro-thiazine-4-carboxylate and 1,1 g of 7-(imidazol-1-yl)heptanoic acid in 25 ml of ethyl acetate was added with 1,5 g of dicyclohexylcarbodiimide. After 12 hours the precipitated N,N-dicyclohexylurea was filtered off and the organic phase was extracted with 2N sulfuric acid. The combined aqueous extracts were alkalinized to ph 9,5 and extracted with ethyl ether. From the combined ether organic phases, after the usual working, 2,5 g of ethyl 2-(4-allyloxyphenylthio-methyl)-3[7(-imidazol-1-yl)heptanoyl]-2H-tetrahydro-thiazine-4-carboxylate was obtained, which was then hydrolyzed with 5% aqueous potassium carbonate in ethanol (25 ml) for 30 minutes at 45° C. to obtain, after neutralization with a $NaH_2PO_4$ solution and filtration, 1,9 of 2-(4-allyloxyphenylthiommethyl)-3[7(imidazol-1-yl)heptanoyl]-4-carboxy-2H-tetrahydro-thiazine.

EXAMPLE 19

Using in the procedure of example 4 ethyl 2-(4-alloxyphenylthiomethyl)thiazolidine-4-carboxylate, 2-(4-alloxyphenylthiomethyl)-3[2(imidazol-1-yl) acetyl]-4-carboethoxy-thiazolidine was prepared which was then hydrolyzed with aqueous potassium carbonate to 2-(4-allyloxyphenylthiomethyl)-3-[imidazol-1-yl)acetyl]-4-carboxy-thiazolidine.

EXAMPLE 20

A solution of 2-(4-ethoxycarbonyl-methoxy-phenoxymethyl)-thiazolidine (5,6 g) in 35 ml of ethyl acetate was added to a solution of 2,2 g of potassium carbonate in water and with outside cooling to 5°–10° C., the strongly stirred mixture was added with a solution of 2,25 ml of α-chloroacetyl chloride in a few ml of ethyl acetate. After 2 hours, the organic phase was separated to give, after the usual working, 6,4 g (2-(4-ethoxycarbonylmethoxyphenoxymethyl)-3-chloroacetylthiazolidine.

Using the above compound in the process of examples 6 and 11, the following compounds were prepared:
2-(4-ethoxycarbonylmethoxyphenoxymethyl)-3[2-imidazol-1-yl)acetyl]-thiazolidine;
2-(4-ethoxycarbonylmethoxyphenoxymethyl)-3-[2[β-pyridylmethylthio]acetyl]thiazolidine;
which, after saponification gave the following acids, respectively:
4[3(-imidazol-1-yl)acetyl-thiazolidine-2-yl] methoxy-phenoxyacetic acid
4[3(3'-pyridylmethylthio)acetyl-thiazolidine-2-yl]methoxyphenoxyacetic acid.

EXAMPLE 21

Using 2-(imidazol-1-yl)ethylamine in the procedure of example 10, N-2-[imidazol-1-yl]ethyl, N'-[2(4,methoxyphenoxymethyl)-thiazolidine-3-yl]-malonodiamide was obtained.

EXAMPLE 22

Using in the procedure of Example 13 respectively 2-(4-ethoxycarbonyl-methoxy-phenoxymethyl]-thiazolidine, N-β-pyridylmethyl-2-carboxy-acetamide and N-2(imidazol-1-yl)ethyl-2-carboxyacetamide, the following compounds were prepared:
1-N-(3'-pyridylmethyl), 3-N[2'(4''-ethoxycarbonylmethoxyphenoxymethyl)-thiazolidin-3-yl]-malonodiamide;
1-N(3'-pyridylmethyl), 3-N[2'(4''-carboxy-methoxyphenoxymethyl)-thiazolidin-3yl]-malonodiamide;
1-N-[2'-(imidazol-1-yl)ethyl, 3-N[2'(4''-ethoxycarbonylmethoxyphenoxy)-thiazolidin-3'-yl]-malonodiamide;
1-N-[2'-(imidazol-1-yl)ethyl, 3-N[2'(4''-carboxymethoxyphenoxymethyl)-thiazolidin-3'-yl]-malonodiamide.

EXAMPLE 23

Using in the process of Example 13 2-(4-methoxyphenoxymethyl)-1,3-thiazolidine, 2-(4-methoxyphenoxymethyl)-2H-tetrahydro-thiazine e N-β-pyridylmethyl-monosuccinoyl-amide, the following compounds were prepared:
1N-(β-pyridylmethyl)-3N'[2'(4''-methoxyphenoxymethyl)-thiazolidin-3'-yl]-succinoyldiamide;
1N-(β-pyridylmethyl)-3N'[2'(4''-methoxyphenoxymethyl)-2'H-tetrahydro-thiazine-3'-yl]-succinoyldiamide.

EXAMPLE 24

To a solution of 2-(4-methoxyphenoxymethyl)-thiazolidine (2,8 g) in ethyl acetate (60 ml) under strong stirring and cooling to 0°–8° C., a solution of potassium bicarbonate (1,4 g) in water (5 ml) was added, then, during 15 minutes, a solution of 3-ethoxycarbonyl-propionyl chloride (2,2 ml) in ethyl acetate. After 2 hours the organic phase was separated to give, after the usual working, 3,2 g of 2-(4-methoxyphenoxymethyl)-3-[3-ethoxycarbonyl]propionylthiazolidine.

We claim:
1. A compound of the formula

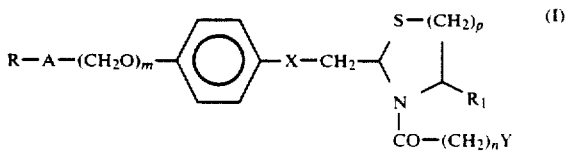

wherein R is $CO_2Ra$;
$R_1$ is H or $CO_2Ra$;
A is a single bond, cis or trans HC=CH, C≡C, $CH_2$ 1 or $CH_2$—$CH_2$;
Y is a substituent selected from the group consisting of —$H_1$—CO—Re, —$CO_2Ra$, —$CONRbRc$, imidazol-1-yl, 3-pyridyl, —$X_1(CH_2)n$—Rd; and

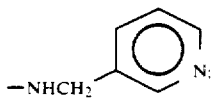

Ra is hydrogen or $C_1$-$C_5$ or straight or branched alkyl;

Rb and Rc are H, $C_1$-$C_5$ alkyl, 2-dimethylamino-ethyl, 2-diethylamino-ethyl,

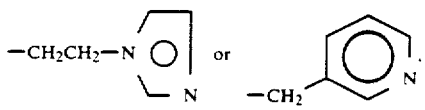

or taken together with the nitrogen atom to which they are bound form a 4-($C_1$-$C_5$-alkyl)piperazin-yl ring;

Rd is hydrogen, $C_1$-$C_5$ straight or branched alkyl,

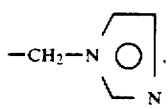

3-pyridyl, $CO_2Ra$ or $CONRbRc$;
Re is $C_1$-$C_5$ straight or a branched alkyl or phenyl;
X and $X_1$ are independently oxygen or sulfur;
m is zero or 1;
n is an integer 1 to 7;
and p is 1; and
pharmaceutically acceptable acid or base addition salts thereof, enantiomers, racemates or diastereoisomers thereof, or mixtures thereof.

2. A compound according to claim 1, wherein the group R—A—$(CH_2O)_m$— represents carboxyl, ethoxycarbonyl, ethoxycarbonylmethoxy, methoxycarbonylvinyl or carboxymethoxy; $R_1$ is carboxyl, methoxycarbonyl or ethoxycarbonyl; and Y represents ethoxycarbonyl, N-β-pyridylmethylamido, N-imidazol-1-yl-ethyl-amido, N-methylamido, N-methyl-piperazinyl-carbonyl, β-pyridylmethylthio, imidazol-1-yl-ethylthio, acetylthio, ethylthio or 1-imidazolyl.

3. A cytoprotective composition comprising a cytoprotective amount of a compound according to claim 1 in admixture with a pharmaceutically acceptable carrier.

4. A cytoprotective composition comprising a cytoprotective amount of a compound according to claim 2 in admixture with a pharmaceutically acceptable carrier.

5. A method for protecting tissues in an animal which comprises administering to the animal a cytoprotective amount of a compound according to claim 1.

6. A compounds of the formula

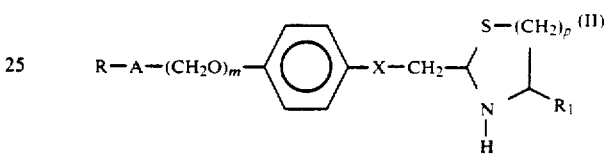

wherein R is $COORa$;
$R_1$ is a H or $COORa$,
A is a single bond, cis or trans CH—CH, C≡C, $CH_2H$ or $CH_2CH_2$;
Ra is hydrogen or $C_1$-$C_5$ straight or branched alkyl;
X is oxygen or sulfur;
m is zero or 1; and
p is 1.

* * * * *